US011160925B1

United States Patent
Ly et al.

(10) Patent No.: US 11,160,925 B1
(45) Date of Patent: Nov. 2, 2021

(54) AUTOMATIC DRUG DELIVERY SYSTEM FOR DELIVERY OF A GLP-1 THERAPEUTIC

(71) Applicant: Insulet Corporation, Acton, MA (US)

(72) Inventors: Trang Ly, Concord, MA (US); Matt Rainville, Boxford, MA (US); M. Thomas Andersen, Highland, UT (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 17/179,984

(22) Filed: Feb. 19, 2021

Related U.S. Application Data

(60) Provisional application No. 63/143,437, filed on Jan. 29, 2021.

(51) Int. Cl.
| | |
|---|---|
| A61M 5/172 | (2006.01) |
| A61M 5/142 | (2006.01) |
| A61M 5/14 | (2006.01) |
| A61K 38/28 | (2006.01) |
| A61K 38/26 | (2006.01) |

(52) U.S. Cl.
CPC ........... *A61M 5/1723* (2013.01); *A61K 38/26* (2013.01); *A61K 38/28* (2013.01); *A61M 5/1408* (2013.01); *A61M 5/14248* (2013.01); *A61M 2205/502* (2013.01); *A61M 2205/52* (2013.01); *A61M 2205/8206* (2013.01); *A61M 2230/201* (2013.01)

(58) Field of Classification Search
CPC ............ A61M 5/1723; A61M 5/14276; A61M 5/14248; A61M 5/14244; A61M 5/172; A61M 5/2448; A61M 5/24; A61M 5/20; A61M 5/31568; A61M 31/002; A61M 5/142; A61M 5/19; G16H 20/17; A61K 38/28; A61K 38/26; A61B 5/14532; A61B 5/4839
See application file for complete search history.

(56) References Cited

U.S. PATENT DOCUMENTS

| | | | |
|---|---|---|---|
| 2014/0054883 A1* | 2/2014 | Lanigan ............ | A61M 39/1011 285/33 |
| 2015/0361154 A1* | 12/2015 | Jowett .................... | A61K 38/26 514/6.5 |
| 2018/0207357 A1* | 7/2018 | John ...................... | G16H 20/17 |
| 2019/0240417 A1 | 8/2019 | Hostettler et al. | |
| 2020/0197605 A1* | 6/2020 | Haidar ................ | A61M 5/1723 |

* cited by examiner

*Primary Examiner* — Manuel A Mendez
(74) *Attorney, Agent, or Firm* — Kacvinsky Daisak Bluni PLLC

(57) ABSTRACT

The disclosed embodiments are directed to a wearable automatic drug delivery device configured to provide basal dosing of GLP-1 or co-formulation of GLP-1 and insulin. The size and frequency of the basal doses may be controlled by a medication delivery algorithm resident on the wearable drug delivery device based on a basal dosing history and readings from a continuous glucose monitor monitoring the glucose levels of the wearer of the device.

15 Claims, 6 Drawing Sheets

← Side Effect Mode

Side Effect Mode is designed to reduce side effects such as nausea or other gastrointestinal side effects. Enter this mode to suspend or reduce delivery of the GLP-1 Therapeutic for a default period of time (30 minutes) or enter a user-defined period of time.

FIG. 4C

← Side Effect Mode

Use Side Effect Mode during when experiencing negative side effects of the GLP-1 Therapeutic, for example, nausea.

Side Effect Mode will stop or reduce the delivery of the GLP-1 Therapeutic for the time specified below. Choose any time between 15 minutes and 3 hours.

Duration
15 min. to 3 hrs.

_____ Hrs., _____ Min.

FIG. 4D

AUTOMATIC DRUG DELIVERY SYSTEM FOR DELIVERY OF A GLP-1 THERAPEUTIC

CROSS-REFERENCE TO RELATED APPLICATIONS

This application claims the benefit of the filing date of U.S. Provisional Application Ser. No. 63/143,437, filed Jan. 29, 2021, the entire contents of which are incorporated herein by reference in their entirety.

BACKGROUND

Glucagon Like Peptide 1 receptor agonists (GLP-1s) for the treatment of Type 2 diabetes first entered the market in 2005 and their use has grown significantly since that time. GLP-1s are known as an efficacious tool to reduce blood glucose levels and lower body weight, while providing cardiovascular benefits for people living with type 2 diabetes. The GLP-1 receptor agonists currently approved in the United States for the treatment of type 2 diabetes include exenatide (administered twice daily via a pen), liraglutide and lixisenatide (administered once daily via a pen), and once-weekly agents exenatide extended-release, albiglutide, semiglutide and dulaglutide, all delivered via a pen.

GLP-1s drive favorable efficacy via several unique mechanisms which have benefits for diabetes management. In particular, and most importantly, GLP-1s lower the glucose levels in the patient. In addition, they tend to suppress post-prandial glucagon release, delay stomach emptying, and increase insulin sensitivity. Additionally, GLP-1 receptor agonists can help with weight loss and result in less hypoglycemia when used in combination with insulin. As disclosed in this application, using a fixed-ratio treatment of GLP-1 and insulin via continuous subcutaneous infusion can increase patient use and further improve glycemic control.

There are several reasons why Type 2 patients have a low adherence to or tend to discontinue therapy altogether. The process of transitioning to an injectable therapy is challenging and a significant milestone for both patients and HCPs. Patients tend to resist the idea of moving beyond oral therapies as injections are often perceived by the patient as a signal for a worsening disease state. In addition, GLP-1s are well known for their unpleasant gastrointestinal side effects, often causing the patient to experience nausea. To reduce the severity of these adverse events, medication dosing can be slowly titrated, but side effects remain. Nausea is the most common adverse effect reported within the GLP-1 class, affecting up to 50% of users. This negatively impacts patient adherence and creates additional labor for the HCP practice in the form of both clinical support and patient counseling. Following adverse gastrointestinal events, the method and frequency of administration precludes many patients from beginning and staying on therapy.

A number of systems provide basal delivery of drugs, such as GLP-1, insulin, chemotherapy drugs, pain management drugs and the like. Throughout a day, the basal insulin needed for a diabetic user to maintain a stable fasting glucose target setting varies 20-30% or more at different times. Thus, it is important that the basal delivery of the drugs be based on a time-dependent basal profile learned by the system based on various histories regarding the delivery of the drug to the patient.

DEFINITIONS

As used herein, the term "GLP-1 Therapeutic" is defined to include formulations of GLP-1 and co-formulations of GLP-1 and insulin, in any concentrations.

As used herein, the term "drug" is defined to include GLP-1 Therapeutics, insulin, chemotherapy drugs, pain relief drugs (e.g., morphine), blood pressure medication, hormones, methadone, and any other single drug or combination thereof to be administered in liquid form.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The co-infusion of a GLP-1 Therapeutic has advantages over the infusion of insulin alone. Infusing large doses of insulin has a side effect of promoting weight gain for the patient. The use of a GLP-1 Therapeutic dramatically reduces the quantity of insulin required to maintain the correct elevated glucose levels in the patient, and, as a result, the susceptibility for weight gain, and/or the weight gain already experienced by the patient, may be reduced. Further, due to the manner in which GLP-1 acts in the human body, for example, by suppressing post-prandial glucagon release and delaying stomach emptying, GLP-1 has a tendency to promote weight loss which may tend to overcome or eclipse the potential for weight gain prompted by the use of large amounts of insulin. The combination of infusing both GLP-1 and insulin together could potentiate glucose-lowering effects while minimizing the unwanted side effects of nausea and weight gain.

In a preferred embodiment, the GLP-1 Therapeutic includes a co-formulation of GLP-1 and rapid-acting insulin, but not long-acting insulin. There are particular advantages to using rapid-acting insulin instead of long-acting insulin in a co-formulation with GLP-1. GLP-1 receptor agonists stimulate insulin secretion and inhibit glucagon secretion, thereby lowering blood glucose levels. Given this known mechanism, it is expected that a co-formulation with rapid-acting insulin, given in response to rising glucose levels, as disclosed herein, would be more effective and have a greater glucose lowering effect than a co-formulation with long-acting insulin could provide without glucose feedback (e.g., via a CGM). The co-formulation delivered by continuous or basal subcutaneous infusion would work synergistically to reduce fasting hyperglycemia as well as post-prandial glucose excursions, as the co-formulation is being delivered in a more physiological manner compared to delivery of a long-acting insulin or a co-formulation including long-acting insulin, which would be delivered, for example, once weekly, given the nature and intended use a long-acting insulin. Further, incretins are naturally released after eating and therefore the advantageous mode of delivery of a GLP-1 Therapeutic disclosed herein more closely emulates physiological responses, i.e., larger amounts (e.g., bolus) of GLP-1 Therapeutic are delivered upon food consumption and smaller amounts (e.g., basal) of GLP-1 Therapeutic are delivered when fasting or not consuming food.

In one aspect of the invention, a drug delivery system that includes a memory and a controller is provided that provides the patient with basal doses of GLP-1 Therapeutic. The memory may store programming code and a basal dose history and may be configured to execute the programming code. Execution of the programming code may configure the controller to titrate the GLP-1 Therapeutic continuously or in small amounts over an extended period of time, to reduce the likelihood of the patient experiencing negative side effects (e.g., nausea). This is contrary to conventional methods for delivering GLP-1 alone to a patient, for example all at once and via a pen.

In another aspect of the invention, size, and timing of each basal dose of the GLP-1 Therapeutic may be varied by the programming code. In another aspect of the invention, the programming code may act to vary the size and timing of each basal dose based on a reading from a sensor which may include, for example, a continuous glucose monitoring (CGM) sensor providing readings of the patient's glucose level. In yet another aspect of the invention, the programming code may act to interrupt the basal delivery of the GLP-1 Therapeutic when the user indicates onset of a negative side effect related to the basal delivery of the GLP-1 Therapeutic, and the system may thereafter automatically ramp up and/or resume delivery of basal doses of the GLP-1 Therapeutic. In yet another aspect of the invention, the programming code can provide larger doses at different times of the day, for example, after the patient has eaten a meal. Delivering the GLP-1 Therapeutic in this fashion and according to exemplary embodiments disclosed herein has the benefit of delaying stomach emptying via the GLP-1 receptor agonist and addressing an increase in blood glucose via the insulin, resulting in a combined beneficial impact that may not result from delivery of a GLP-1 receptor agonist alone or insulin alone.

In one embodiment of the invention, the drug delivery system may be pre-filled with the GLP-1 Therapeutic. In other embodiments of the invention, the reservoir may be fillable by the patient with co-formulations of GLP-1 and insulin that come pre-mixed in a single container or vial at a particular ratio of GLP-1:insulin, or in separate containers or vials, wherein the containers/vials of GLP-1 or insulin can be, for example, a pen, syringe or glass vial and wherein the user fills the reservoir from each container/vial to achieve a particular ratio of GLP-1 to insulin and which is tailored to the particular patient. In yet another embodiment of the invention, the drug delivery device may be configured with two reservoirs, one containing GLP-1 and the other containing insulin, such that the co-formulation of GLP-1 and insulin may be varied by programming code on the drug delivery device or a separate controller on-the-fly.

In one embodiment, the device may be configured to deliver a time-dependent basal dose of GLP-1 Therapeutic based on an adaptable profile. In one aspect of the invention, a method is disclosed that includes retrieving a basal delivery history that is a collection of basal delivery dosages of the GLP-1 Therapeutic delivered according to a basal delivery schedule. The basal delivery history may include a predetermined number of basal delivery dosages of the GLP-1 Therapeutic delivered over a period of time. The period of time may be further partitioned into intervals that span a time range less than the period of time. The delivery schedule may include a particular delivery time for each basal delivery dosage during each respective interval, and each basal delivery dosage is an amount of the GLP-1 Therapeutic delivered at the particular delivery time, wherein each particular delivery time is one point in time during the interval. The controller may process the basal delivery dosages in the period of time to remove short term fluctuations of the basal delivery dosages. The processed basal delivery dosages within each interval may be evaluated to obtain an interval profile for each of the intervals. The interval profile is a data structure including the amount of the GLP-1 Therapeutic delivered in each processed basal delivery dosage and the particular delivery time associated with each processed basal delivery dosage. In the example method, each processed basal delivery dosage may be analyzed at each particular delivery time in each interval profile for an interval and for every interval during the period of time. From the analysis, an average interval profile may be determined. The average interval profile may contain a series of average basal delivery dosages where each average basal delivery dosage in the series has a corresponding average delivery time. The controller may iteratively evaluate each average basal delivery dosage in the series with respect to other average basal delivery dosages in the series to determine a similarity in the amount of the GLP-1 Therapeutic delivered and a similarity in the corresponding average delivery time. Based on results of the evaluating, aggregating average basal delivery dosages meeting an amount similarity threshold may be aggregated and a time range related to an aggregation of delivery times of the aggregated average basal delivery dosage may be assigned based on a time similarity threshold. The basal delivery schedule may be modified with an updated amount of the GLP-1 Therapeutic to be delivered as an updated basal delivery dosage based on the aggregated average basal delivery dosages, and an updated delivery time based on the assigned time range. The process may cause delivery of respective updated basal delivery dosages by the controller according to the modified basal delivery schedule via a pump mechanism communicatively coupled to the controller.

In another aspect, a process is disclosed that includes accessing a basal delivery history of the GLP-1 Therapeutic, a bolus delivery history of the GLP-1 Therapeutic, a blood glucose measurement history, and a meal announcement history for a period of time from a memory coupled to the controller. The basal delivery history is a data structure containing amount data related to basal doses of the GLP-1 Therapeutic delivered at respective times over the course of the basal delivery history based on an algorithm executed by the controller. The bolus drug history is a data structure containing bolus delivery time data related to delivery of bolus doses of the GLP-1 Therapeutic and an amount of the GLP-1 Therapeutic delivered in each bolus dose. The blood glucose measurement history is a data structure of blood glucose measurement values in which each blood glucose measurement value has a corresponding time when the blood glucose measurement value was obtained. The meal announcement history is a data structure of times when a meal announcement notification was received by the controller. Respective data in each of the basal delivery history, the bolus delivery history, the blood glucose measurement history, and the meal announcement history may be filtered by the controller according to predetermined filter settings related to a time interval of the period of time. A daily basal profile may be calculated using the filtered respective data from each of the histories. The daily basal profile may be a time schedule for delivering respective basal delivery dosages that includes times at which a basal delivery dosage is to be delivered. A control signal for delivery of a basal dosage of the calculated basal delivery dosages at a scheduled time from the daily basal profile may be generated by the controller. The control signal may be output to a pump mechanism of the drug delivery system communicatively coupled to the controller causing delivery of a respective basal dosage in the daily basal profile.

BRIEF DESCRIPTION OF THE DRAWINGS

To easily identify the discussion of any particular element or act, the most significant digit or digits in a reference number refer to the figure number in which that element is first introduced.

FIGS. 4A-D illustrate an exemplary user interface for invoking a "Side Effect Mode" wherein the basal delivery of the GLP-1 Therapeutic is reduced or suspended for a period of time in response to a user indication of a negative side effect, for example, nausea.

DETAILED DESCRIPTION

Figure 1A:
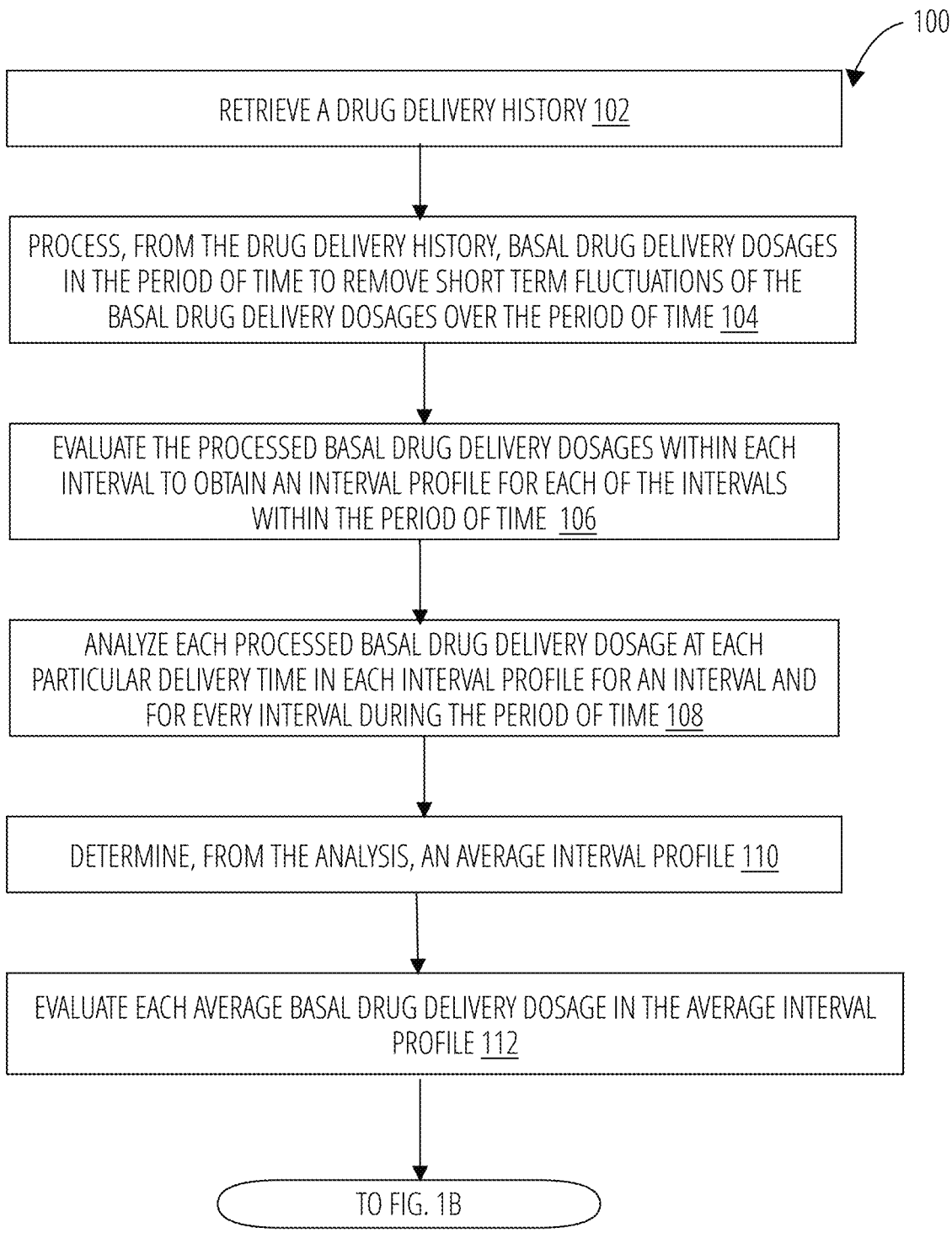
FIGS. 1A and 1B illustrate an example routine utilizing minimal data related to delivery of a drug by a drug delivery system.

Systems, devices, computer-readable medium and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

Various examples provide a method, a system, a device and a computer-readable medium for responding to inputs provided by sensors, such as an analyte sensor, and users of an automatic drug delivery system. The various devices and sensors that may be used to implement some specific examples may also be used to implement different therapeutic regimens using different drugs than described in the specific examples.

In one example, the disclosed methods, system, devices or computer-readable medium may perform actions related to managing a user's blood glucose in response to ingestion of a meal by the user.

The disclosed examples provide techniques that may be used with any additional algorithms or computer applications that manage blood glucose levels and GLP-1 and insulin therapy. These algorithms and computer applications may be collectively referred to as "medication delivery algorithms" or "medication delivery applications" and may be operable to deliver different categories of drugs (or medications), such as diabetes treatment drugs (e.g., GLP-1 Therapeutics), chemotherapy drugs, pain relief drugs, blood pressure medication, hormones, or the like.

A type of medication delivery algorithm (MDA APP) may include an "artificial pancreas" algorithm-based system, or more generally, an artificial pancreas (AP) application. For ease of discussion, the software, computer programs and computer applications that implement the medication delivery algorithms or applications may be referred to herein as an "MDA application" or an "AP application." An AP application may be configured to provide automatic delivery of a GLP-1 Therapeutic based on a blood glucose sensor input, such as signals received from an analyte sensor, such as a continuous blood glucose monitor, or the like. In an example, the artificial pancreas (AP) application, when executed by a processor, may enable monitoring of a user's blood glucose measurement values, determine an appropriate level of the GLP-1 Therapeutic for the user based on the monitored glucose values (e.g., blood glucose concentrations or blood glucose measurement values) and other information, such as information related to, for example, carbohydrate intake, exercise times, meal times or the like, and take actions to maintain a user's blood glucose value within an appropriate range. A target blood glucose value of the particular user may alternatively be a range blood glucose measurement values that are appropriate for the particular user. For example, a target blood glucose measurement value may be acceptable if it falls within the range of 80 mg/dL to 120 mg/dL, which is a range satisfying the clinical standard of care for treatment of diabetes. In addition, an AP application as described herein determine when a user's blood glucose wanders into the hypoglycemic range or the hyperglycemic range.

As described in more detail with reference to the examples of FIGS. 1A-2, an automatic drug delivery system may be configured to implement a method to estimate and update the time-dependent basal profile for a user after a certain period of closed loop operation time (e.g. 14 days). The first example, illustrated in FIG. 1A and FIG. 1B, may only utilize the history of the delivery of the GLP-1 Therapeutic by an AID algorithm. The described processes may be suitable for users who manage their blood glucose within acceptable range (e.g., approximately 0%-15%) of their target blood glucose setting most of the time (e.g., approximately 85%-100%) and bolus their meals accurately most of the time (e.g., approximately 85%-100%). The second example, described with reference to FIG. 2, utilizes all GLP-1 Therapeutic, CGM, and meal information, and tries to compensate for non-ideal meal boluses. The second example may be implemented with fasting blood glucose measurement values that are persistently high/low, and wherein the delivered boluses over/under compensate for meals, in which case the basal delivery dosages are likely to be underestimated or overestimated.

The routine 100 may process the basal delivery history maintained over the certain period of closed loop operation time, which is referred to as a period of time that is maintained as the basal delivery history. This basal delivery history may be stored in a permanent, non-disposable device that may communicate with a disposable pump, such as a smartphone, a personal diabetes management (PDM) device or stored on the cloud and downloaded to be utilized in the embodiments within this application. The basal delivery history may, for example, include a predetermined number of basal delivery dosages of a GLP-1 Therapeutic delivered over a period of time. In the examples, the basal delivery history may be a collection of basal delivery dosages delivered according to a basal delivery schedule. The schedule may, for example, include a particular delivery time for each basal delivery dosage during each respective interval (e.g., deliveries every hour, 60 minutes, 30 minutes, or the like).

In the examples, a period of time may be a month, a number of months, week, or a number of weeks less than or longer than a month, a day, a number of days, a number of hours, such as 72, 84 or 96, or the like. In routine 100, the period of time may be further partitioned into a number of intervals and each interval may span a time range less than the period of time. For example, an interval may be a day, a week, a certain number of days, such as 3, 5, a certain number of hours, such as 6, 12, 24, 36, 72 or the like, or another interval of time, which is less than the period of time. A day equals 24 hours in these examples. For example, the period of time may be two weeks, the interval may be a day, and the day may be further segmented into respective times, such as 2-hour increments. In addition, each basal delivery dosage in the collection may be an amount of the GLP-1 Therapeutic delivered at the particular delivery time during each respective interval and each particular delivery time is one point in time during the interval. The particular delivery time may correspond to a respective time (t).

In block 102, a controller on a wearable drug delivery device, when implementing routine 100, may be configured and operable to retrieve the basal delivery history from a memory coupled to the controller. The controller and memory are shown in another example.

In block 104, routine 100 enables the controller to process the basal delivery dosages from the basal delivery history in the period of time to remove short term fluctuations of the basal delivery dosages over the period of time. For example, a low pass filter with a cutoff frequency of 0.14 mHz (1 cycle/2 hours) may be applied to the data a(t) from the basal delivery history to eliminate discrepancies or outliers in the data. The respective basal delivery history may be divided into 14 24-hour (1-day) intervals and processed by the controller using the low pass filter.

In block 106, routine 100 evaluates the respective processed basal delivery dosages within each interval to obtain an interval profile for each of the intervals within the period of time. The interval profile may, for example, be a data structure with a number of entries that includes, for each entry, an amount of the GLP-1 Therapeutic delivered in each processed basal delivery dosage and the particular delivery time associated with each processed basal delivery dosage during the interval.

In some examples, an average basal delivery dosage for each particular time within the basal delivery history may be calculated. For example, each particular basal delivery dosage delivered at the particular delivery time within each interval in the period of time may be averaged to obtain the estimate of a daily basal profile. In the example, the filtering cutoff frequency of (1 cycle/2 hours) reduces the 24 hours of the period of time into 12 2-hour intervals, which may be referred to as basal profile intervals. Each of the 12 individual basal profile intervals that are identified based on the processed data from the basal delivery history may include an amount of the GLP-1 Therapeutic delivered via the basal dosage during that interval, and basal profile intervals with defined amounts of the GLP-1 Therapeutic within a certain threshold (such as 0.05U~0.25U) may be clustered to provide a smaller number of intervals (e.g., 3 4-hour intervals) in the daily basal profile that can be more easily utilized by the users for their personal diabetes treatment applications.

In an example, the period of time may be 1 week and the interval may be 1 day. Each 1-day interval may be further segmented into times (t), which may be increments of 1 hour, 2 hours, 5, 10, 20 or 30 minutes or the like. In one example, the daily basal profile may initially contain the average basal delivery for each 2-hour period within a given day, in which case the time (t) increments are 2 hours.

In block 108, the controller, while executing routine 100, may analyze each processed basal delivery dosage at each particular delivery time in each interval profile for an interval and for every interval during the period of time. For example, a basal dosage of the GLP-1 Therapeutic may be administered every 5 minutes over the course of an interval (e.g., a day, 24 hours, 12 hours or the like). The amount of the basal dosage (e.g., 0.5 Units of a GLP-1 Therapeutic) and the time of delivery (e.g., 0600) may be stored. The intervals, such as days, may be differentiated in a memory of a wearable drug delivery device based on an activation time of the wearable drug delivery device. For example, the wearable drug delivery device may have a clock or a counter that starts at the activation time, which may be at 8 am on the first day.

In block 110, routine 100 determines, from the analysis, an average interval profile, which contains a series of average basal delivery dosages, wherein each average basal delivery dosage in the series has a corresponding average particular delivery time. The average basal delivery dosages may be the average amount of the GLP-1 Therapeutic delivered as a basal dosage at a particular time (e.g., a time t, such as 7 AM during an interval (e.g., 24 hour period-1 day)) over the entire basal delivery history. For example, due to the filtering, the 24 hour period of the interval may be segmented into 12 particular times that are separated by 2 hours (e.g., the particular time t=1 may be 7 am, the particular time t=2 would be 9 am, and the particular time t=3 would be 11 am, and so on). The average delivery dosage for particular time between t=1 and t=2 in each interval may be 0.05 U, the average delivery dosage for particular time between t=2 and t=3 in each interval may also be 0.05 U, while average delivery dosage for the particular time between t=3 to the end of the day in each interval may be 0.25 U.

In block 112, the controller, when implementing routine 100, may be configured to evaluate, iteratively, each average basal delivery dosage in the series of average basal delivery dosages with respect to other average basal delivery dosages delivered at different times in the series to determine a similarity in the amount of the GLP-1 Therapeutic delivered and a similarity in the corresponding average particular delivery time. Continuing with the numerical example, the controller may determine the similarity in the amount of the GLP-1 Therapeutic delivered at particular times t=1 and t=2 is 1.0 while the similarity in the amount of drug delivered at times t=2 and t=3 is 0.20 or the like. The similarity of each delivery between segments can be compared by evaluating the % change in amount of GLP-1 Therapeutic delivered. For instance, in the numerical example, the change in GLP-1 Therapeutic delivery from 1.0 between t=1 and t=2, versus 0.2 from t=2 and t=3, the similarity is thus 0.2/1.0=20%. means the % change, and thus the "similarity" is −80%. The routine 100 continues to FIG. 1B.

Figure 1B:
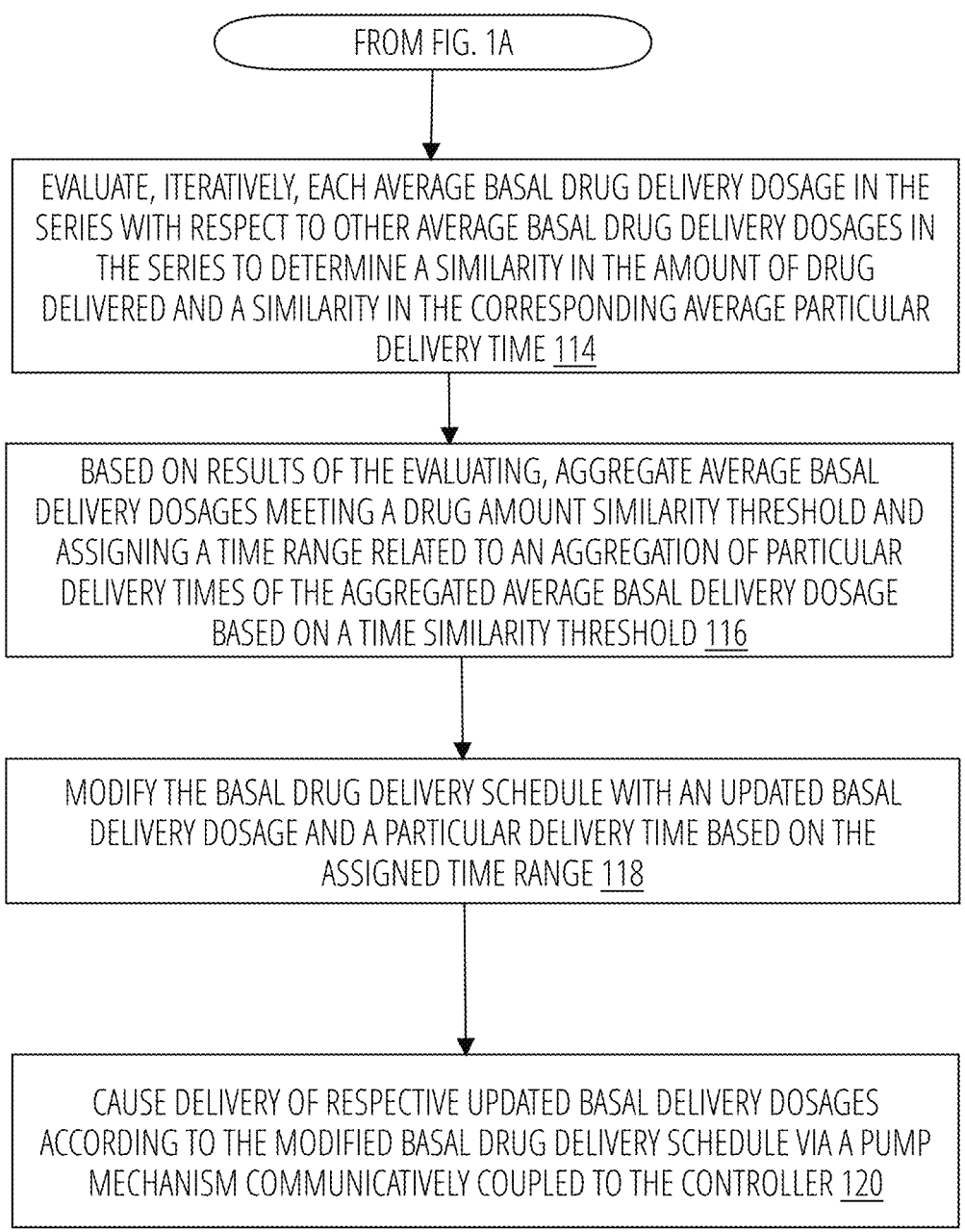

In FIG. 1B, as shown in block 114, the controller may be further configured, when executing the routine 100, and, based on results of the evaluating, to aggregate the average basal delivery dosages that meet an amount similarity threshold. The average GLP-1 Therapeutic similarity threshold may be based on a percentage of the average amounts being compared, such as within 5%, 10% or the like. In addition, a time range related to an aggregation of particular delivery times of the aggregated average basal delivery dosage may be assigned based on the time similarity threshold. The time similarity threshold may also be a percentage of the segmented time. For example, if the time segment is 2 hours (120 minutes), the time threshold may be 5%, 10% or the like, which means the time similarity threshold may be 6 minutes, 12 minutes or the like. This aggregated average basal delivery dosage, in an example, may be a sum of an amount of the GLP-1 Therapeutic delivered at the first corresponding average particular delivery time and an amount of the GLP-1 Therapeutic delivered at the second corresponding average particular delivery time based on the time threshold. Alternatively, the controller may use a clustering algorithm on the average basal delivery dosages that are close in range of a respective amount similarity threshold and a time delivery threshold.

In an example, the controller may be configured to combine a first average basal delivery dosage from a first corresponding average particular delivery time (e.g., between t=1 and t=2) with a second average basal delivery dosage from a second corresponding average particular delivery time (e.g., between t=2 and t=3). The combining of the first average basal delivery dosage and the second average basal delivery dosage provides the updated basal delivery dosage. For example, the average basal dosages of 0.05 U at particular time between t=1 and t=2 as well as between t=2 and t=3 may be aggregated as 0.10 U between t=1 and t=3. In addition, the controller may be further configured to combine the first average particular delivery time with the second average particular delivery time. For example, the particular time may be aggregated to provide an aggregate time of 4 hours. This results in an aggregate average delivery dosage of 0.1U over 4 hours in this numerical example.

In block 116, the controller may modify the basal delivery schedule with an updated amount of the GLP-1 Therapeutic to be delivered as an updated basal delivery dosage based on the aggregated average basal delivery dosages, and an updated particular delivery time based on the assigned time range. In addition, the controller may set, for a new interval for which the modified basal delivery schedule is to be applied, a start time of the updated basal delivery dosage that corresponds to the updated particular delivery time.

The controller, at block 118, may cause delivery of respective updated basal delivery dosages according to the modified basal delivery schedule via a pump mechanism (shown in another example) communicatively coupled to the controller. For example, the controller may generate an activation control signal at the start time in a new interval to expel the updated basal delivery dosage from a reservoir. The new interval being a day in the modified basal delivery schedule. The generated activation signal may be output to a pump mechanism coupled to the reservoir and the controller (as described with reference to FIG. 3).

The example routine 100 is implemented utilizing data from the basal delivery history alone because of the consistent blood glucose measurement values of the particular individual. However, other individuals that may need more flexibility may rely on an algorithm that inputs additional data when determining an adjusted basal need.

Figure 2:
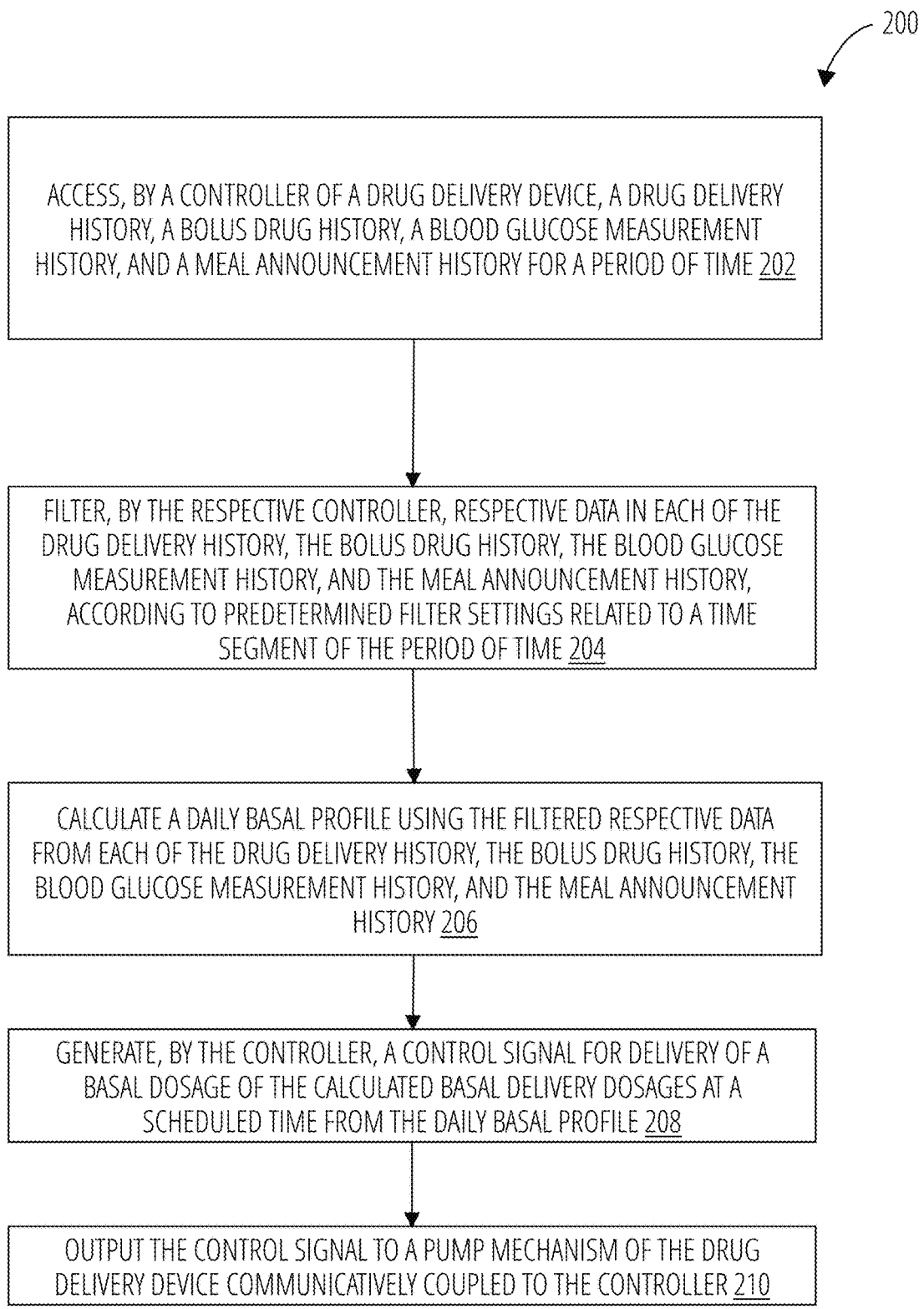
FIG. 2 illustrates another example routine utilizing multiple different sets of data related to delivery of a drug by a drug delivery system.

FIG. 2 illustrates a routine 200 in accordance with another example of the disclosed subject matter. The routine 200 provides additional robustness by utilizing data from different histories of the user.

In block 202, a controller of a drug delivery device, when executing programming code that implements routine 200, may be configured to access in a memory coupled to the controller a basal delivery history, a bolus delivery history, a blood glucose measurement history, and a meal announcement history for a period of time.

In the example of routine 200, the basal delivery history may be a data structure containing GLP-1 Therapeutic amount data related to basal doses of the GLP-1 Therapeutic delivered at respective times over the course of the basal delivery history based on an algorithm executed by the controller. For example, the GLP-1 Therapeutic amount data may be related to a GLP-1 Therapeutic and may be in units of GLP-1 Therapeutic, such as 0.5 Units (U), 0.25 U, 0.05 U or the like, and a time of the delivery may be stored as a respective time for each delivery, such as 0500 (5 am), 0346 (5:25 am), 0700 (7 am), 1345 (1:45 pm), 1900 (7 pm) or the like. Alternatively, other drugs may be administered. Because the basal delivery history tracks background or basal doses deliveries of the drug, the basal delivery history may have multiple deliveries (e.g., 1-20 instances) and relatively small amounts of the GLP-1 Therapeutic (in comparison to the bolus dosages) delivered (e.g., 0.5 U versus 30.0 U) per each instance throughout an interval.

The bolus delivery history may, for example, be a data structure containing bolus delivery time data related to delivery of bolus doses of the GLP-1 Therapeutic and an amount of the GLP-1 Therapeutic delivered in each bolus dose. For example, the bolus delivery history may be arranged similar to the basal delivery history and may have an amount of the GLP-1 Therapeutic delivered.

In addition, the blood glucose measurement history may, for example, be a data structure of blood glucose measurement values (blood glucose measurement values) in which each blood glucose measurement value has a corresponding time when the blood glucose measurement value was obtained. For example, the data structure may have a blood glucose measurement value in one column, such as 120 mg/dL, and in another column a time, such as 0600 (6 am), or the like.

In some examples, the controller may access the meal announcement history, which, may be, for example, a data structure of times when a meal announcement notification was received by the controller. In some examples, the meal announcement notification may be received from a user interface device, such as a switch, push button, keyboard, touchscreen display, a microphone, or the like. The controller may, for example, store the meal announcement notification with a time that the notification was received, for example, the meal announcement notification may be a binary indication, such as Yes or No, or some other type of flag, and the time associated with the meal announcement notification may be a time, such as 0600 (6 AM), 1200 (12 PM) and 1800 (6 PM), or the like. At a time when a meal announcement is not received, the controller may set the indication to No and log the time which corresponds to other times stored in the other data structures for the basal delivery history, bolus delivery history, and the blood glucose measurement history.

In block 204, the controller when executing routine 200 filters respective data in each of the basal delivery history, the bolus delivery history, the blood glucose measurement history, and the meal announcement history, according to predetermined filter settings related to a time interval of the period of time. For example, a low pass filter with a cutoff frequency of approximately 0.14 millihertz (1 cycle/2 hours) may be applied to the respective data in each of the basal delivery history (which may be referred to as a(t)), the bolus delivery history (which may be referred to as b (t)), the blood glucose measurement history (which may be referred to as g(t)), and the meal announcement history (which may be referred to as m(t)). The controller may be configured to divide the filtered data into 14 24-hour (1-day) periods. In other examples, cutoff frequencies other than 1 cycle/2 hours may be chosen, such as 1 cycle/3 hours or the like. Furthermore, the filters for the bolus delivery history, the blood glucose measurement history, and the meal announcement history may be chosen with different shapes and durations to match the expected insulin/meal absorption curves, insulin-on-board (IOB)/carbohydrates-on-board (COB) curves, or the like.

In block 206, routine 200 calculates a daily basal profile using the filtered respective data from each of the basal delivery history, the bolus delivery history, the blood glucose measurement history, and the meal announcement history. The daily basal profile may be, for example, a time schedule for delivering respective basal delivery dosages and times at which a basal delivery dosage is to be delivered. The respective basal delivery dosages and times in the daily basal profile may correspond to a respective adjusted basal need calculated for a respective time in the interval.

The example process at block 206 may include the controller determining a series of time settings for times in the time schedule based on the predetermined filter settings from block 204. For example, each time in the series of time settings may be selected based on the time interval (i.e., interval) of the period of time. The controller may access a memory to obtain an amount of the drug from the drug amount data in the basal delivery history a(t) and at a time (t) in the amount data that corresponds to each time in the series of time settings. The amount of the GLP-1 Therapeutic from time t may be referred to as a "GLP-1 Therapeutic basal delivery history factor" for the respective time t. The controller may further be configured to obtain, from the bolus delivery history b (t), a respective amount of the GLP-1 Therapeutic delivered in a bolus dose at each time (t) in the series of time settings. The controller may be further configured to determine a number of blood glucose measurement factors from blood glucose measurement values g(t) in the blood glucose measurement history and that corresponds to a respective time (t) in the series of time settings. Based on these calculated factors (i.e., delivery history factors, blood glucose measurement factors, the bolus delivery history factor), a basal dose of the GLP-1 Therapeutic may be determined.

In block 208, routine 200 generates, by the controller, a control signal for delivery of a basal dosage at a scheduled time from the daily basal profile.

In block 210, routine 200 causes the controller to output the control signal to a pump mechanism of the drug delivery device communicatively coupled to the controller.

In other examples, the calculation of the daily basal profile at block 206 may be performed using different processes. An adjusted basal need may be an individual entry in the daily basal profile. The adjusted basal need may, in one example, be obtained based on a number of different factors as discussed in the respective examples below.

In other examples, the controller may be configured to account for additional data that is collected based on the assumption that a user is not paying close attention to blood glucose measurement values, in which case the adjusted basal need discussed above may be used in combination with other factors. The controller may determine the adjusted basal need according to different equations depending upon the example. The respective equations may utilize different factors, such as a delivery history factor obtained from the basal delivery history, a bolus factor obtained from the bolus delivery history, a blood glucose measurement factor obtained from the blood glucose measurement history, and a meal announcement factor based on a meal announcement history. In other examples, a proportionality factor may be incorporated into the equation to further optimize the basal dosage settings.

For example, the delivery history factor may be an amount of basal GLP-1 Therapeutic delivered at a respective time t taken from the basal delivery history. The amounts of the basal GLP-1 Therapeutic delivered in the basal delivery history a(t).

In another example, the controller may be configured to determine a blood glucose measurement factor for each respective time (i.e., t) of a number of preselected times from the blood glucose history. For example, the controller may obtain, by accessing a memory, a blood glucose measurement value from the blood glucose measurement history stored in the memory that corresponds to the respective time (t). The controller, in the example, may use the respective time (t) in the following equation to determine the blood glucose measurement factor:

$$\frac{g(t) - 120}{DIA \cdot CF} \qquad \text{Eq. (1)}$$

where:
g(t) is the blood glucose measurement value from the blood glucose measurement history at the respective time (t);
the value 120 is a fasting blood glucose target setting;
DIA is the duration of GLP-1 Therapeutic action (e.g., 3 hours or the like); and
CF is the estimated correction factor (e.g., estimated using the rule 1800/TDI).

In evaluating Eq. (1), the controller may determine a numerator, specific to the respective time (t) of the preselected times, by subtracting the fasting blood glucose target setting from the obtained blood glucose measurement value g(t) corresponding to the respective time. The denominator may be determined by multiplying a duration of insulin action (DIA) value by an estimated correction factor. The denominator may remain constant over the period of time, such as two weeks, but may be updated based on changes to a user's physical attributes (e.g., the consistency of blood glucose measurement value) or habits (e.g., diet or physical activity).

In Eq. (1), the estimated correction factor CF may be an estimate of a specific user's sensitivity to the GLP-1 Therapeutic and how efficiently the user processes the GLP-1 Therapeutic. The fasting blood glucose target setting in this example is 120, but different values may also be used, such as 115 mg/dL, 130 mg/dL, 140 mg/dL or the like. In some examples, the fasting blood glucose target setting may be user dependent. For example, the controller may obtain the fasting blood glucose target setting from user preference settings (described with reference to a later example) or from a clinical setting common for the physical attributes (e.g., height, weight, age, resting heart rate and/or the like) of the user that are stored in the memory accessible by the controller. Alternatively, it may be obtained from clinical data sources and input into the memory coupled to the controller.

For example, the controller may determine individual adjusted basal need for each respective time (t) in the daily basal profile based on the blood glucose measurement factor that corresponds to each time in the series of time settings may be calculated, for example, using the obtained blood glucose measurement value (g(t)), a fasting blood glucose target setting (e.g., 120), a duration of insulin action value (DIA), and a correction factor (CF).

In addition, the controller may also determine a meal announcement factor that corresponds to each time in the series of time settings based on the meal announcement history. The controller may also determine a drug ratio related to meal content in which the drug ratio related to meal content may be a GLP-1 Therapeutic-to-carbohydrate ratio. The meal announcement factor may be determined by retrieving a meal announcement value corresponding to a respective time in the series of time settings. In the example, the meal announcement value may be an estimate of a number of grams of carbohydrates in the meal that triggered a particular meal announcement notification. A meal announcement notification may be received via user input, an automatic meal detection algorithm, historical data or the like. For example, the estimated number of grams of carbohydrates may be input by the user via a user interface to a drug delivery device. Alternatively, the estimated number of carbohydrates may be determined by a meal detection algorithm that utilized historical data of changes in blood glucose measurement values to generate a meal announcement notification. In another alternative, a meal detection algorithm may utilize inputs from various sensors (e.g., camera or microphone, global positioning sensors) and computer applications (e.g., calendar applications, travel direction applications, recipe applications, or the like). Based on one or more of the meal detection or meal announcement processes, the controller may determine or estimate a GLP-1 Therapeutic-to-carbohydrate ratio. The controller may use the GLP-1 Therapeutic-to-carbohydrate ratio (GC) as the divisor in a division operation in which the numerator is the meal announcement value, the quotient of the division may be referred to as the meal announcement factor. For example, an equation (Eq. (2)) for the meal announcement factor may be:

$$m(t)/GC \qquad \text{Eq. (2)}$$

where:
m(t) is the meal announcement value; and
GC is the GLP-1 Therapeutic-to-carbohydrate ratio.

In these more detailed calculations, the adjusted basal need of routine 1 may have been calculated utilizing only the obtained amount of the GLP-1 Therapeutic from the basal delivery history a(t). However, as more factors are used in the routine 200, the controller may, for example, determine "an aggregate factor." The controller may be configured to sum the obtained amount of the GLP-1 Therapeutic from the basal delivery history a(t) from the amount data, the respective blood glucose measurement factor, and the obtained respective amount of the GLP-1 Therapeutic delivered in the bolus dose to provide the aggregate factor. The aggregate factor, in this example, for a respective time (t) may generally refer to the sum of values from the respective time (t) in the basal delivery history and the bolus delivery history, and the blood glucose measurement factor based on the respective time (t). For example:

$$\text{Aggregate Factor}(t) = a(t) + \frac{g(t) - 120}{DIA \cdot CF} + b(t) \qquad \text{Eq. (3)}$$

where:
t is a respective time;
a(t) is the obtained amount of the GLP-1 Therapeutic from the amount data delivered via basal dosages in the basal delivery history at the respective time; and
the term g(t)−120/DIA·CF in the aggregate factor(t) may be, as mentioned above, the "blood glucose measurement factor" at the respective time (t).

In an alternative example, during the steps of block 206, the controller may be configured to determine the number of blood glucose measurement factors from the blood glucose measurement history using different techniques in different examples. In the specific example, the controller may be operable to calculate an adjusted basal need for each respective time (t) in the daily basal profile using the following equation:

$$\underset{\text{Need }[a_{adj}(t)]}{\text{Adjusted Basal}} = \text{Drug Delivery History Factor} \qquad \text{Eq. (4)}$$

$$[a(t)] +$$

Blood Glucose Measurement $$\text{Factor}\left[\frac{g(t) - 120}{DIA \cdot CF}\right] +$$

Bolus History Factor [b(t)] −

Meal Announcment Factor $$\left[\frac{m(t)}{GC}\right]$$

where:
(t) is a preselected time of the interval with the interval set as 24 hours or 1 day;
the delivery history factor, blood glucose measurement factor and bolus delivery history factor are collectively referred to as the "aggregate factor" explained above;
the meal announcement factor is based on an estimated number of grams (referred to as "number") of carbohydrates in a meal that triggered a meal announcement m(t) at respective time (t); and
GC is the estimated GLP-1 Therapeutic-to-carbohydrate ratio (e.g., estimated using the rule 800/TDI).

In the example, each calculated adjusted basal need may be an individual entry in the schedule. For example, the controller may be configured, for each respective time of the plurality of preselected times, to provide an aggregate factor, which is a sum of the obtained amount of the GLP-1 Therapeutic at the respective time, the obtained respective amount of the GLP-1 Therapeutic delivered in the bolus dose, and the respective blood glucose measurement factor. The controller is further configured to subtract from the aggregate factor the meal announcement factor from the respective time and output the result of the summing and subtracting as the adjusted basal need for a respective time (t) of the plurality of preselected times.

In yet another example of calculating the adjusted basal need for the time schedule of the daily basal profile as part of the processing at block 206, the adjusted basal need for a respective time of the number of preselected times may be determined using another process that accounts for the user's correction bolus $b_c(t)$ at respective time t that may be associated with meal ingestions depending on the user's use cases. The drug delivery device may be manually commanded by the user to deliver the correction bolus. Alternatively, or in addition, the controller may, based on user preference settings, be permitted to deliver the correction bolus. In one exemplary embodiment, correction boluses $b_c(t)$ can also be processed with a low pass filter having a cutoff frequency of approximately 0.14 mHz or another cutoff frequency setting. A proportion X of these manual correction bolus $b_c(t)$ may be considered to be relevant to meals and subtracted to address the user's basal needs with further specificity.

For example, the controller may be configured to determine the adjusted basal need for each respective time of the number of preselected times, based on the following equation:

$$a_{adj}(t) = a(t) + \frac{g(t) - 120}{DIA \cdot CF} + b(t) - \frac{m(t)}{GC} - X \cdot b_c(t) \qquad \text{(Eq. 5)}$$

where:

(t) is a preselected time of the interval with the interval set as 24 hours or 1 day;

the value 120 is an example of the target fasting blood glucose setting (which may be different for different users);

DIA is the duration of GLP-1 Therapeutic action (e.g. 3 hours);

CF is the estimated correction factor (e.g. 1800/TDI);

GC is the estimated GLP-1 Therapeutic-to-carb ratio (e.g. 800/TDI);

$b_c(t)$ is the correction bolus of the user; and

X may be a proportionality factor.

In one example, the proportionality factor X may be considered 0.5, which is an assumption that half of the manual boluses used by the user over the course of the interval may be associated with meals (e.g., the user manually attempting to compensate for meal consumption). Of course, values other than 0.5 may be set for the proportionality factor X, such as 0.3, 0.55, or the like. Users who exhibit keto diets may assume a lower proportionality factor than 0.5, as they may not need a significant amount of the GLP-1 Therapeutic associated with meals. Users who are highly active may not need as much of the GLP-1 Therapeutic associated with basal delivery and may assume a higher proportionality factor than 0.5. This value can be potentially fixed to an individualized value per user and per recommendation from the physician, adjusted occasionally by the user and/or the physician manually, or adjusted every fixed period of time, such as 3-14 days, or adjusted automatically based on the proportion of GLP-1 Therapeutic delivery as basal versus bolus in the available basal delivery history every fixed period of time.

In yet another example, rather than subtracting the GLP-1 Therapeutic deliveries from the aggregate factor as described in the equations above, the summation of all GLP-1 Therapeutic deliveries can be adjusted by a proportion of bolus GLP-1 Therapeutic deliveries versus the automated GLP-1 Therapeutic deliveries. Allowances may be made to more heavily bias towards an equal split between basal GLP-1 Therapeutic delivery needs and bolus GLP-1 Therapeutic delivery needs.

In this example, the controller may access a memory to obtain an amount of the GLP-1 Therapeutic from the amount data in the basal delivery history (a(t)) and at a time (t) (which is a respective time or may be the "time interval") in the amount data that corresponds to each time in the series of time settings. The controller may further be configured to obtain, from the bolus delivery history (b(t)), a respective amount of the GLP-1 Therapeutic delivered in a bolus dose at each time (t) in the series of time settings. The controller may be further configured to determine a number of blood glucose measurement factors from blood glucose measurement values (g(t)) in the blood glucose measurement history and that corresponds to a respective time (t) in the series of time settings. Each respective blood glucose measurement factor (g(t)) of the number of blood glucose measurement factors may correspond to a respective time (t) in the series of time settings. The controller may be further configured to calculate a blood glucose measurement factor that corresponds to each time in the series of time settings using the obtained blood glucose measurement value, a fasting blood glucose target setting, a duration of GLP-1 Therapeutic action (DIA) value, and an estimated correction factor (CF). All of the factors below may be calculated as described with reference to the examples of FIGS. 1A-2 above.

In this specific example, the routine 200 may configure the controller, when determining the adjusted basal need for each of the number of preselected times, to summing the obtained amount of the GLP-1 Therapeutic, the respective blood glucose measurement factor, and the obtained respective amount of the GLP-1 Therapeutic delivered in the bolus dose to provide an aggregate factor. The controller may determine a proportion of an amount of the GLP-1 Therapeutic provided via bolus dosages to an amount provided via the aggregate factor. The proportion may be modified based on a contribution factor.

In more detail, the controller may implement the following equation, and based on a(t), b(t), and g(t), the total GLP-1 Therapeutic $a_{tot}(t)$ may be calculated (in a manner similar to the aggregate factor above) as:

$$a_{tot}(t) = a(t) + \frac{g(t) - 120}{DIA \cdot CF} + b(t)$$

In an example, the amount of GLP-1 Therapeutic delivery for basal needs (referred to as $a_b(t)$ (below)) can be estimated based on the proportion of bolus versus total GLP-1 Therapeutic as:

$$a_b(t) = a_{tot}(t) \cdot \text{(contribution factor)}$$

where the contribution factor may be a weighting factor that can range between approximately 0.25 to approximately 0.75, or approximately 0.0 to approximately 1.0, depending on the overall proportion of the GLP-1 Therapeutic delivery for boluses versus total delivery.

In more detail, the contribution factor may be determined:

$$\text{contribution factor}(t) = \left(0.25 + 0.5 \cdot \frac{b(t)}{a_{tot}(t)}\right)$$

The total GLP-1 Therapeutic $a_{tot}(t)$ (referred to as "the aggregate factor" in earlier examples) may be multiplied by the modified proportion to determine a resultant. The controller may be configured to output the resultant of the multiplying of $a_{tot}(t)$ and contribution factor as the adjusted basal need for a respective time of the plurality of preselected times.

The foregoing examples described a daily basal profile or a time schedule. The respective daily basal profile or time schedule may be the same for every day of the week. However, it is further envisioned that the controller may be configured to evaluate more broadly than single day and modify basal based on day of week, or day of year, such as large meals on Friday night or Sunday morning; or intense exercise on Saturdays, for example.

It may be helpful to describe an example of a system that may be configured to implement the above described examples as well as additional examples.

Figure 3:
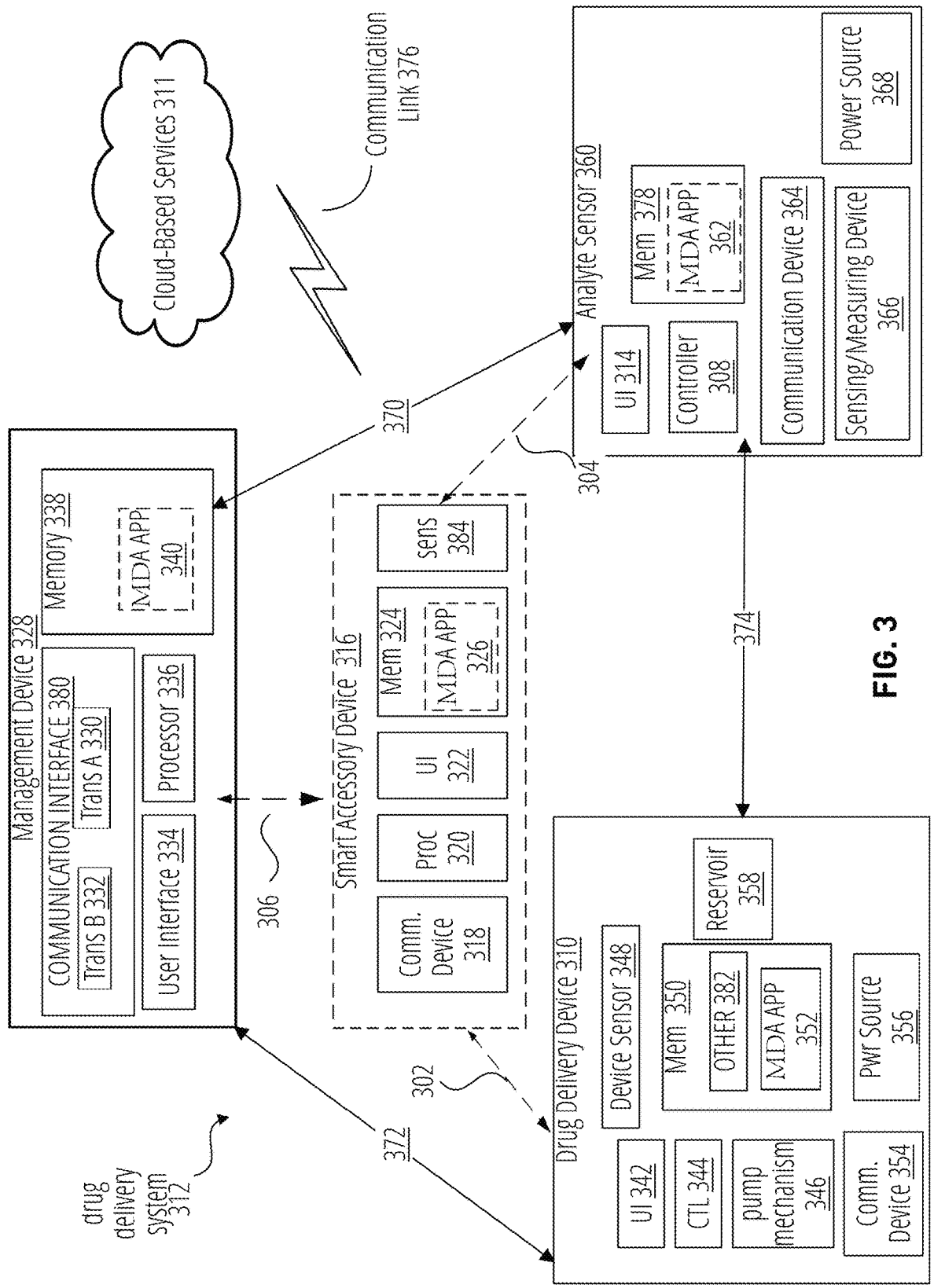
FIG. 3 illustrates an example drug delivery system suitable for implementing the example routines of FIGS. 1A-2 as well as other example routines or processes in accordance with the disclosed embodiments.

FIG. 3 illustrates a functional block diagram of an exemplary drug delivery system suitable for implementing the example processes and techniques described herein.

The drug delivery system 312 may implement (and/or provide functionality for) a medication delivery algorithm, such as an artificial pancreas (AP) application, to govern or control automated delivery of GLP-1 Therapeutic to a user (e.g., to maintain euglycemia—a normal level of glucose in the blood). The drug delivery system 312 may be an automated drug delivery system that may include a wearable automatic drug delivery device 310, an analyte sensor 360, and a management device (PDM) 328. The drug delivery system 312 may be an automatic drug delivery system that is configured to deliver a dosage of the GLP-1 Therapeutic without any user interaction, or in some examples, limited user interaction, such as depressing a button to announce ingestion of a meal or the like.

The system 312, in an optional example, may also include a smart accessory device 316, such as a smartwatch, a personal assistant device or the like, which may communicate with the other components of system 312 via either a wired or wireless communication links 302-306.

The management device 328 may be a computing device such as a smart phone, a tablet, a personal diabetes management device, a dedicated diabetes therapy management device, or the like. In an example, the management device (PDM) 328 may include a processor 336, a management device memory 338, a user interface 334, and a communication device 380. The management device 328 may contain analog and/or digital circuitry that may be implemented as a processor 336 for executing processes based on programming code stored in the management device memory 338, such as the AP algorithm or application (APP) 340, to manage a user's blood glucose levels and for controlling the delivery of the drug, medication, or therapeutic agent according to a time schedule, basal drug profile, and the like as discussed above. The management device 328 may be used to initially set up, adjust settings, and/or control operation of the wearable automatic drug delivery device 310 and/or the analyte sensor 360 as well as the optional smart accessory device 316.

The processor 336 may also be configured to execute programming code stored in the management device memory 338, such as the MDA APP 340. The MDA APP 340 may be a computer application that is operable to deliver the GLP-1 Therapeutic based on information received from the analyte sensor 360, the cloud-based services 311 and/or the management device 328 or optional smart accessory device 316. The memory 338 may also store programming code to, for example, operate the user interface 334 (e.g., a touchscreen device, a camera or the like), the communication device 380 and the like. The processor 336 when executing the MDA APP 340 may be configured to implement indications and notifications related to meal ingestion, blood glucose measurements, and the like. The user interface 334 may be under the control of the processor 336 and be configured to present a graphical user interface that enables the input of a meal announcement, adjust setting selections and the like as described above.

In a specific example, when the memory 338 stores an MDA APP, such as an artificial pancreas application, the processor 336 may also be configured to execute a diabetes treatment plan (which may be stored in the memory 338) that is managed by the MDA APP 340 stored in memory 338. In addition to the functions mentioned above, when the MDA APP 340 is an AP application, it may further provide functionality to enable the processor 336 to determine a basal dosage according to an adjusted basal need, a basal profile or the like as described with respect to the examples of FIGS. 1A-2. In addition, the MDA APP 340 provides functionality to enable the processor 336 to output signals to the wearable automatic drug delivery device 310 to deliver the basal GLP-1 Therapeutic dosages described with reference to the examples of FIGS. 1A-2.

The communication device 380 may include one or more transceivers such as Transceiver A 332 and Transceiver B 330 and receivers or transmitters that operate according to one or more radio-frequency protocols. In the example, the transceivers 332 and 330 may be a cellular transceiver and a Bluetooth® transceiver, respectively. For example, the communication device 380 may include a transceiver 332 or 330 configured to receive and transmit signals containing information usable by the MDA APP 340.

The drug delivery device 310, in the example system 312, may include a user interface 342, a controller 344, a pump mechanism 346, a communication device 354, a memory 350, a power source 356, device sensors 348, and a reservoir 358. The wearable automatic drug delivery device 310 may be configured to perform and execute the processes described in the examples of FIGS. 1A-2 without input from the management device 328 or the optional smart accessory device 316.

The controller 344 alone may implement the processes of FIGS. 1A, 1B and FIG. 2 to determine a daily basal profile or an adjusted basal need as described with respect to the other examples, based on an input from the analyte sensor 360. The controller 344 of the wearable automatic drug delivery device 310 may be operable to implement delivery of the GLP-1 Therapeutic to the user according to a diabetes treatment plan or other delivery regimen stored in the memory 350 as other programs 382 (Other). For example, the controller 344 may be operable to execute programming code and be configured when executing non-transitory programming code of a medication delivery application or algorithm, such as MDA APP 340 and other programs 382, to perform the functions that implement the example routines and processes described herein. In an operational example, the controller 344, when executing the programming code implementing MDA APP 340, may be configured to output a control signal causing actuation of the drive mechanism 346 (the drive mechanism 346 may also be referred to as a pump mechanism) to deliver time-dependent basal dosages or the like as described with reference to the examples of FIGS. 1A-2.

The memory 350 may store programming code executable by the controller 344. The programming code, for example, may enable the controller 344 to control expelling the GLP-1 Therapeutic from the reservoir 358 and control the administering of doses of the GLP-1 Therapeutic based on signals from the MDA APP 352 or, external devices, when the drug delivery device 310 is configured to receive and respond to the external control signals. The memory 350 may also be configured to store other data and programming code, such as other programs 382. For example, the memory may be configured to store the data structures discussed above with respect to the examples of FIGS. 1A-2 with data, such as the basal delivery history, bolus delivery history, a blood glucose measurement history and a meal announcement history, a correction bolus delivery history as well as data related to the time-dependent basal dosages, such as a daily basal profile, or a time schedule. In some instances, all glucose and GLP-1 Therapeutic histories are stored in the management device 328, which may be a smartphone, or smart accessory 307, and the cloud-based services 311, which may include data storage. The drug delivery device 310 and CGM upload their histories to the management device 328, when in communication. The management device 328, in turn uploads the histories to the cloud-based services 311 periodically. When the drug delivery device 310 or analyte sensor 360 is disposed of, no history will be lost because the respective history is stored in the cloud by cloud-based services 311. Similarly, when a management device 328 or smart accessory 307 is replaced, no history will be lost. The basal profile adaptive computation as discussed in the example routines 1 and 2 may be performed on the management device 328 and transmitted to the drug delivery device 310 at activation of the drug delivery device 310 via a communication link, such as 372 or 302. Alternatively, the computation can be done in the cloud, downloaded to the management device 328, and then transmitted to the pod when activated.

The reservoir 358 may be configured to store the GLP-1 Therapeutic suitable for automated delivery.

The device sensors 348 may include one or more of a pressure sensor, a power sensor, or the like that are communicatively coupled to the controller 344 and provide various signals. In an example, the controller 344 or a processor, such as 336, may be operable to use the various signals in the determination of an amount of the GLP-1 Therapeutic delivered, a daily basal profile or an adjusted basal need as described with respect to the other examples. In such an example, the controller 344 may have a clock, a counter or the like that maintains or enables maintaining a time. An initial time may be set when the wearable drug delivery device 310 is initially set up by a user or HCP.

In an example, the wearable automatic drug delivery device 310 includes a communication device 354, which may be a receiver, a transmitter, or a transceiver that operates according to one or more radio-frequency protocols, such as Bluetooth, Wi-Fi, a near-field communication standard, a cellular standard, or the like. The controller 344 may, for example, communicate with a personal diabetes management device 328 and an analyte sensor 360 via the communication device 354.

The wearable automatic drug delivery device 310 may be attached to the body of a user, such as a patient or diabetic, at an attachment location and may deliver, according to an automatic delivery algorithm, any therapeutic agent, including any drug or medicine, such as the GLP-1 Therapeutic or the like, to a user at or around the attachment location. A surface of the wearable automatic drug delivery device 310 may include an adhesive to facilitate attachment to the skin of a user as described in earlier examples. The controller 344 may be operable to maintain a basal delivery history of the delivered therapeutic drug, such as the GLP-1 Therapeutic, by storing delivered basal dosages and bolus dosages in memory 350. The memory 350 may also store a basal delivery history that may be a data structure containing amount data related to background doses of the GLP-1 Therapeutic delivered at respective times in the basal delivery history, a bolus delivery history that may be a data structure containing bolus delivery time data related to delivery of bolus doses of the GLP-1 Therapeutic and an amount of the GLP-1 Therapeutic delivered in each bolus dose, a blood glucose measurement history that may be a data structure of blood glucose measurement values in which each blood glucose measurement value has a corresponding time when the blood glucose measurement value was obtained, and a meal announcement history that may be a data structure of times when a meal announcement notification was received by the controller.

The wearable automatic drug delivery device 310 may, for example, include a reservoir 358 for storing the GLP-1 Therapeutic, a patient interface (not shown), for example, a needle or cannula, for delivering the drug into the body of the user (which may be done subcutaneously, intraperitoneally, or intravenously), and a drive mechanism 346 for transferring the GLP-1 Therapeutic from the reservoir 358 through a needle or cannula and into the user. The drive mechanism 346 may be fluidly coupled to reservoir 358, and communicatively coupled to the controller 344.

The wearable automatic drug delivery device 310 may further include a power source 356, such as a battery, a piezoelectric device, other forms of energy harvesting devices, or the like, for supplying electrical power to the drive mechanism 346 and/or other components (such as the controller 344, memory 350, and the communication device 354) of the wearable automatic drug delivery device 310.

In some examples, the wearable automatic drug delivery device 310 and/or the management device 328 may include a user interface 334, respectively, such as a keypad, a touchscreen display, levers, light-emitting diodes, buttons on a housing of the management device 328, a microphone, a camera, a speaker, a display, or the like, that is configured to allow a user to enter information and allow the management device 328 to output information for presentation to the user (e.g., alarm signals or the like). The user interface 334 may provide inputs, such as a voice input, a gesture (e.g., hand or facial) input to a camera, swipes to a touchscreen, or the like, to processor 336 which the programming code interprets.

When configured to communicate to an external device, such as the PDM 328 or the analyte sensor 360, the wearable automatic drug delivery device 310 may receive signals over the wired or wireless link 594 from the management device 328 or 374 from the analyte sensor 360. The controller 344 of the wearable automatic drug delivery device 310 may receive and process the signals from the respective external devices (e.g., cloud-based services 311, smart accessory device 316, or management device 328) to implement delivery of a drug to the user according to a daily basal profile, a time schedule, a modified basal drug delivery schedule stored in the memory 350 as other programs 382 (Other).

In an operational example, the controller 344, when executing the MDA APP 340, may output a control signal operable to actuate the drive mechanism 346 to deliver a carbohydrate-compensation dosage of the GLP-1 Therapeutic, a correction bolus, a revised basal dosage or the like as described with reference to the examples of FIGS. 1A-2.

The smart accessory device 316 may be, for example, an Apple Watch®, other wearable smart device, including, for example, eyeglasses, provided by other manufacturers, a global positioning system-enabled wearable, a wearable fitness device, smart clothing, or the like. Similar to the management device 328, the smart accessory device 316 may also be configured to perform various functions including controlling the wearable automatic drug delivery device 310. For example, the smart accessory device 316 may include a communication device 318, a processor 320, a user interface 322, a sensor 384, and a memory 324. The user interface 322 may be a graphical user interface presented on a touchscreen display of the smart accessory device 316. The sensor 384 may include a heart rate sensor, a blood oxygen saturation sensor, a pedometer, a gyroscope, a combination of these sensors, or the like. The memory 324 may store programming code to operate different functions of the smart accessory device 316 as well as an instance of the MDA APP 326. The processor 320 that may execute programming code, such as the MDA APP 326 for controlling the wearable automatic drug delivery device 310 to implement the FIGS. 1A-2 examples described herein.

In an operational example, the drug delivery device 310 may be configured, when the controller 344 executes programming code stored in the memory, such as other programs 382 and MDA APP 352, to obtain, from the basal delivery history stored in the memory, basal drug dosage data. The obtained basal drug dosage data obtained from the basal delivery history may include information related to a plurality of basal dosages delivered daily over a number of weeks. The controller may process the obtained basal dosage data using a low pass filter to reduce any outlier data points that may skew an average of the amounts of the GLP-1

Therapeutic delivered during a basal dosage. For example, the controller may be further configured to identify basal dosages within a same day of the processed basal dosage data that have similar amounts of the GLP-1 Therapeutic delivered in a basal dosage; and aggregate the identified basal dosages to reduce a number of different basal dosages to be accounted for in the daily basal profile. The drug delivery device 310 may generate from the processed basal dosage data, a daily basal profile that includes a number of basal dosages and a respective time for each of the basal dosages of the number of basal dosages to be delivered during a day. The controller may generate a control signal according to the daily basal profile. The controller may apply the control signal to the pump mechanism to deliver a respective basal dosage at the basal dosages respective time in the daily basal profile.

In addition to the above operational example, the controller 344 may be operable or configured to execute programming code embodying the routine 100 of FIGS. 1A-1B and routine 200 of FIG. 2.

The analyte sensor 360 may include a controller 308, a memory 378, a sensing/measuring device 366, a user interface 537, a power source/energy harvesting circuitry 534, and a communication device 364. The analyte sensor 360 may be communicatively coupled to the processor 336 of the management device 328 or controller 344 of the wearable automatic drug delivery device 310. The memory 378 may be configured to store information and programming code, such as an instance of the MDA APP 362.

The analyte sensor 360 may be configured to detect multiple different analytes, such as lactate, ketones, uric acid, sodium, potassium, alcohol levels, hormone levels, or the like, and output results of the detections, such as measurement values or the like. The analyte sensor 360 may, in an example, be configured to measure a blood glucose value at a predetermined time interval, such as every 5 minutes, or the like. The communication device 364 of analyte sensor 360 may have circuitry that operates as a transceiver for communicating the measured blood glucose values to the management device 328 over a wireless link 370 or with wearable automatic drug delivery device 310 over the wireless communication link 374. While called an analyte sensor 360, the sensing/measuring device 366 of the analyte sensor 360 may include one or more additional sensing elements, such as a glucose measurement element a heart rate monitor, a pressure sensor, or the like. The controller 308 may include discrete, specialized logic and/or components, an application-specific integrated circuit, a microcontroller or processor that executes software instructions, firmware, programming instructions stored in memory (such as memory 378), or any combination thereof.

Similar to the controller 344, the controller 308 of the analyte sensor 360 may be operable to perform many functions. For example, the controller 308 may be configured by the programming code stored in the memory 378 to manage the collection and analysis of data detected the sensing and measuring device 366.

Although the analyte sensor 360 is depicted in FIG. 3 as separate from the wearable automatic drug delivery device 310, in various examples, the analyte sensor 360 and wearable automatic drug delivery device 310 may be incorporated into the same unit. That is, in various examples, the sensor 360 may be a part of the wearable automatic drug delivery device 310 and contained within the same housing of the wearable automatic drug delivery device 310 (e.g., the sensor 360 or, only the sensing/measuring device 366 and memory storing related programming code may be positioned within or integrated into, or into one or more components, such as the memory 350, of, the wearable automatic drug delivery device 310). In such an example configuration, the controller 344 may be able to implement the process examples of FIGS. 1A-2 alone without any external inputs from the management device 328, the cloud-based services 311, the optional smart accessory device 316, or the like.

The communication link 376 that couples the cloud-based services 311 to the respective devices 310, 360, 328 or 316 of system 312 may be a cellular link, a Wi-Fi link, a Bluetooth link, or a combination thereof. Services provided by cloud-based services 311 may include data storage that stores anonymized data, such as blood glucose measurement values, basal delivery history, bolus delivery history, time data, and other forms of data. In addition, the cloud-based services 311 may process the anonymized data from multiple users to provide generalized information related to clinical diabetes-related data and the like.

The wireless communication links 374, 302, 372, 306, 594 and 370 may be any type of wireless link operating using known wireless communication standards or proprietary standards. As an example, the wireless communication links 374, 302, 372, 306, 594 and 370 may provide communication links based on Bluetooth®, Zigbee®, Wi-Fi, a near-field communication standard, a cellular standard, or any other wireless protocol via the respective communication devices 380, 318, 354 and 364.

In some instances, the basal GLP-1 Therapeutic may comprise a co-formulation of GLP-1 and insulin and, more specifically, rapid-acting insulin. In certain embodiments of the invention, reservoir 358 in wearable drug delivery device 310 may be prefilled with a co-formulation of GLP-1 and a rapid-acting insulin. Rapid-acting insulin is sold under various tradenames, for example, Humalog®, NovoLog®, Admelog®, Apidra®, Fiasp® and Lyumjev®, among others. The GLP-1 may be, for example, liraglutide, which may be co-formulated with U100 rapid-acting insulin in a ratio of 1.8-5.4 mg/ml of insulin, with the preferred co-formulation of 3.6 mg/ml of insulin. In other examples, the GLP-1 may be lixisenatide or exenatide, which may be co-formulated with U100 rapid-acting insulin in a ratio of 20-60 mg/ml of insulin, with a preferred co-formulation of 40 mg/ml of insulin.

In a preferred embodiment, the GLP-1 Therapeutic includes a co-formulation of GLP-1 and rapid-acting insulin, but not long-acting insulin. Using rapid-acting insulin instead of long-acting insulin in a co-formulation with GLP-1 yields particular advantages. GLP-1 receptor agonists stimulate insulin secretion and inhibit glucagon secretion, thereby lowering blood glucose levels. Given this known mechanism, it is expected that a co-formulation with rapid-acting insulin, given in response to rising glucose levels, as disclosed herein, would be more effective and have a greater glucose lowering effect than a co-formulation with long-acting insulin could provide without glucose feedback (e.g., via a CGM). The co-formulation delivered by continuous or basal subcutaneous infusion would work synergistically to reduce fasting hyperglycemia as well as postprandial glucose excursions, as the co-formulation is being delivered in a more physiological manner compared to delivery of a long-acting insulin or a co-formulation including long-acting insulin, which would be delivered, for example, once weekly given the nature and instructions for use of a long-acting insulin. Further, incretins are naturally released after eating and therefore the advantageous mode of delivery of a GLP-1 Therapeutic disclosed herein more closely emulates physiological responses, i.e., larger amounts (e.g., bolus) of GLP-1 Therapeutic are delivered upon food consumption and smaller amounts (e.g., basal) of GLP-1 Therapeutic are delivered when fasting or not consuming food.

In some embodiments of the invention, reservoir 358 of wearable drug delivery device 310 may be fillable, or in some embodiments refillable, by the user, who may obtain premixed co-formulations of GLP-1 and the rapid-acting insulin and transfer the co-formulation into reservoir 358. In other embodiments of the invention, drug delivery device 310 may comprise a second reservoir (not shown) and second pump mechanism (not shown) wherein reservoir 358 contains GLP-1 and wherein the second reservoir contains the rapid-acting insulin, such that the co-formulation of GLP-1 and insulin may be formulated on the fly under the direction of MDA 352. In yet other embodiments, the user may wear two drug delivery devices 310, with the reservoir 358 of the first drug delivery device 310 filled with GLC-1 and the reservoir 358 of the second drug delivery device 310 filled with the rapid-acting insulin. In such an embodiment, the first and second drug delivery devices 310 would communicate wirelessly with each other to coordinate the co-formulation of GLP-1 and insulin to be delivered to the patient under the direction of MDA 352.

In some embodiments of the invention, the user may be able to signal to drug delivery system 312 that he or she has experienced an adverse event or a side effect (e.g., nausea) using user interface 334 of management device 328, user interface 322 of smart accessory device 316 or user interface 342 of drug delivery device 310. For example, the user may enter a "Side Effect Mode" in which the delivery of the GLP-1 Therapeutic may be suspended or reduced for a predetermined period of time or a user-defined period of time (in either case, e.g., 15 minutes, 30 minutes, 45 minutes, 1 hour, 2 hours, 3 hours, or the like), or until receiving a further input from the user, to allow the user to recover from the adverse effect and will thereafter continue as directed by MDA 352. Such suspension may stop delivery of all basal, or alternatively all basal and bolus, GLP-1 Therapeutic for the period of time (pre-determined or user-defined), or reduce delivery of all basal GLP-1 Therapeutic for the period of time (pre-determined or user-defined) by, for example, 25%, 50%, 75%, or the like. In any case, delivery of the GLP-1 Therapeutic may resume upon expiration of the period of time or may ramp back up to the previous rate of delivery (e.g., the previous basal rate of delivery) of GLP-1 Therapeutic. Such ramp up or restoration of GLP-1 Therapeutic delivery after expiration of the period of time may, for example, occur approximately linearly over a period of time, e.g., 15 minutes, 30 minutes, 45 minutes, 1 hour, 2 hours, 3 hours, or the like, or over a period of time that matches the pre-determined or user-defined period of time. Alternatively, the ramp up may occur immediately upon expiration of the predetermined or user-defined period of time.

Figure 4B:
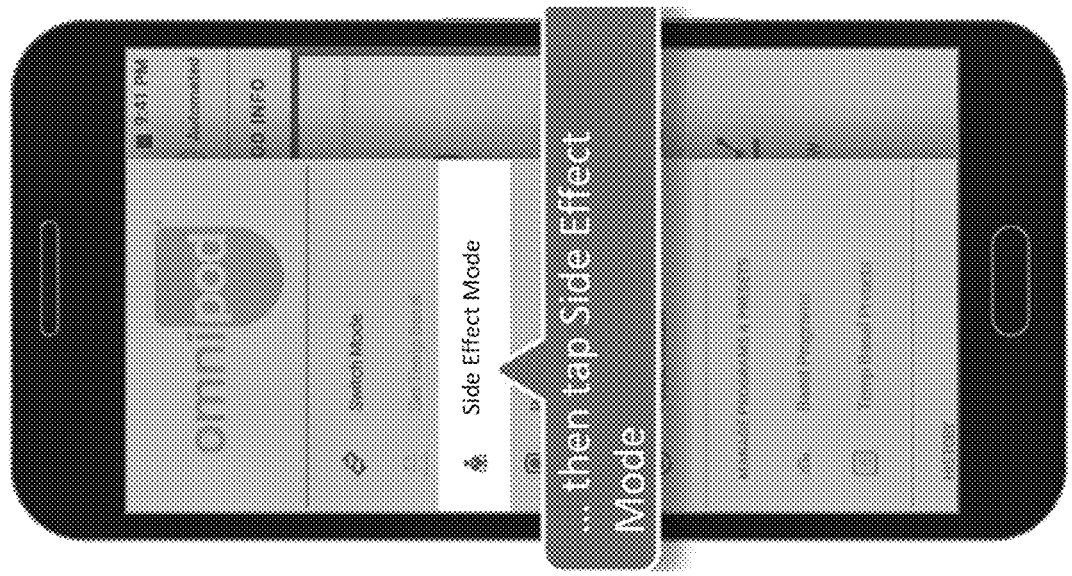
Figure 4A:

FIGS. 4A-4D show exemplary user interface screens for invoking Side Effect Mode and for allowing the user to specify the duration of the suspension of the delivery of the GLP-1 therapeutic. Such screens would appear, for example, as part of user interface 334 or user interface 322, as shown in FIG. 3. Side Effect Mode may be selected from the menu of the main user screen. As shown in FIG. 4A, the user may tap the menu icon which will cause the menu to appear, as shown in FIG. 4B. The user may select the "Side Effect Mode" menu item from the menu. Upon selection of the Side Effect Mode menu item, the user may be delivered to the screen as shown in FIG. 4C which explains the purpose of Side Effect Mode and/or, may be taken to the screen shown in FIG. 4D, wherein the user may enter the duration of the suspension (or reduction in rate) of the delivery of the GLP-1 therapeutic. Although the figures show a duration from 15 minutes to 3 hours, any range of times may be used. Alternatively, the screen shown in FIG. 4C may be shown as part of a series of instructional screens or, for example, a "user manual" built into the user interface. In alternate embodiments of the invention, the user may utilize user interface 342 on drug delivery device 310, as shown in FIG. 3, to invoke Side Effect Mode, in which case, Side Effect Mode may utilize a default duration (e.g., 30 minutes).

Because wearable drug delivery device 310 has controller 344 and a version of MDA 352 running thereon, it may be possible, in certain embodiments, for the user to use drug delivery device 310 independently, without management device 328 or smart accessory device 316. In such cases, drug delivery device 310 may independently communicate with cloud-based services 311 via communication link 376 in addition to analyte sensor 360 via communication link 374.

Software related implementations of the techniques described herein, such as the processes examples described with reference to FIGS. 1A-2 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. Blood glucose measurements may be provided for closed-loop input from a blood glucose monitor, a continuous glucose monitor, or the like. A management device may maintain the data history and adjust or recommend system settings. For example, the disclosed MDA application and algorithms may be operable to perform various functions related to open loop operations, such as the generation of prompts requesting the input of information such as weight or age. Similarly, a dosage amount of insulin may be received by the MDA application or algorithm from a user via a user interface. Other open-loop actions may also be implemented by adjusting user settings or the like in an MDA application or algorithm.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. An automatic drug delivery system comprising:
  a wearable drug delivery device comprising:
    a controller;
    a memory, coupled to the controller and configured to store a basal delivery history;
    software, for execution by the controller, the software implementing a medication delivery algorithm;
    a single reservoir;
    a quantity of a GLP-1 Therapeutic, contained in the single reservoir;
    a pump mechanism, controlled by the medication delivery algorithm and in fluid communication with the single reservoir; and
    a patient interface, in fluid communication with the pump mechanism;
    wherein basal doses of the GLP-1 Therapeutic are delivered to a wearer of the wearable drug delivery device in accordance with a basal delivery schedule, the medication delivery algorithm implementing a method comprising:
      retrieving the basal delivery history, the basal delivery history including a predetermined number of basal dosages of GLP-1 Therapeutic delivered over a period of time partitioned into intervals;
      evaluating the basal dosages within each interval to obtain an interval profile for each interval indicating the amount of GLP-1 Therapeutic delivered in each basal dosage and a delivery time of each basal dosage;
      determining an average interval profile comprising a series of average basal dosages, each having an average delivery time;
      evaluating each average basal dosage with respect to other average basal dosages to determine a similarity in the amount of the GLP-1 Therapeutic delivered and a similarity in the corresponding average delivery time;
      aggregating average basal dosages meeting an amount similarity threshold and assigning a time range based on a time similarity threshold; and
      modifying the basal delivery schedule with an updated amount of the GLP-1 Therapeutic based on the aggregated average basal dosages and an updated delivery time based on the assigned time range.

2. The drug delivery system of claim 1 wherein the medication delivery algorithm can vary the size and timing of the delivery of the doses of the GLP-1 Therapeutic.

3. The drug delivery system of claim 2, further comprising:
  an analyte sensor in communication with the wearable drug delivery device;

wherein the medication delivery algorithm takes as input readings from the analyte sensor to determine the size and timing for delivery of the doses of the GLP-1 Therapeutic.

4. The drug delivery system of claim 3, wherein the analyte sensor is a CGM sensor and further wherein the medication delivery algorithm varies the size and timing for delivery of the doses of the GLP-1 Therapeutic based on the variations in the glucose level of the wearer as detected by the CGM sensor.

5. The drug delivery system of claim 1, wherein the GLP-1 Therapeutic is a co-formulation of liraglutide and a U100 rapid-acting insulin mixed in a ratio of between 1.8 and 5.4 mg of liraglutide per 1 ml of the rapid-acting insulin.

6. The drug delivery system of claim 5, wherein the liraglutide and the rapid-acting insulin are mixed in a ratio of 3.6 mg of liraglutide per 1 ml of the rapid-acting insulin.

7. The drug delivery system of claim 1, wherein the GLP-1 Therapeutic is a co-formulation of lixisenatide or exenatide and a U100 rapid-acting insulin mixed in a ratio of between 20 and 60 mg of lixisenatide or exenatide per 1 ml of the rapid-acting insulin.

8. The drug delivery system of claim 7, wherein the lixisenatide or exenatide and the rapid-acting insulin are mixed in a ratio of 40 mg of lixisenatide or exenatide per 1 ml of the rapid-acting insulin.

9. The drug delivery system of claim 1 wherein:
the wearable drug delivery device further comprises a second reservoir and second pump mechanism coupled to the second reservoir;
the first reservoir contains GLP-1;
the second reservoir contains a rapid-acting insulin; and
the medication delivery algorithm controls the first pump mechanism and the second pump mechanism to provide varying co-formulations of GLP-1 and insulin to a wearer of the wearable drug delivery device.

10. The drug delivery system of claim 1 wherein the medication delivery algorithm is configured to calculate a daily basal profile based on the basal delivery history, a blood glucose measurement history, and a meal announcement history.

11. The drug delivery system of claim 10 wherein the daily basal profile is further based on a bolus delivery history.

12. The drug delivery system of claim 1 wherein the GLP-1 Therapeutic is a co-formulation of GLP-1 and rapid-acting insulin.

13. A wearable drug delivery device comprising:
a controller;
software, for execution by the controller, the software implementing a medication delivery algorithm;
a single reservoir;
a quantity of a GLP-1 Therapeutic, contained in the single reservoir;
a pump mechanism, controlled by the medication delivery algorithm and in fluid communication with the single reservoir; and
a patient interface, in fluid communication with the pump mechanism;
wherein basal doses of the GLP-1 Therapeutic and insulin are delivered to a wearer of the wearable drug delivery device as directed by the medication delivery algorithm; and
wherein the medication delivery algorithm is further configured to:
accept an input from the wearer indicating that the wearer has experienced an adverse event;
suspend delivery of the GLP-1 Therapeutic; and
resume delivery of the GLP-1 Therapeutic after a predetermined period of time or when a further input is received from the wearer indicating that the wearer wishes to resume the delivery.

14. The drug delivery system of claim 1 wherein the wearable drug delivery device is further configured to deliver bolus doses of the GLP-1 Therapeutic.

15. A wearable drug delivery device comprising:
a controller;
software, for execution by the controller, the software implementing a medication delivery algorithm;
a single reservoir;
a quantity of a GLP-1 Therapeutic, contained in the single reservoir;
a pump mechanism, controlled by the medication delivery algorithm and in fluid communication with the single reservoir; and
a patient interface, in fluid communication with the pump mechanism;
wherein basal doses of the GLP-1 Therapeutic are delivered to a wearer of the wearable drug delivery device as directed by the medication delivery algorithm; and
wherein the medication delivery algorithm is further configured to modify a basal delivery schedule for delivery of the GLP-1 Therapeutic based on a history of basal doses.

* * * * *